United States Patent [19]

Kim et al.

[11] Patent Number: 5,416,512
[45] Date of Patent: May 16, 1995

[54] AUTOMATIC THRESHOLD LEVEL STRUCTURE FOR CALIBRATING AN INSPECTION TOOL

[75] Inventors: Douglas Y. Kim, Poughkeepsie; Kurt R. Muller, Hopewell Junction, both of N.Y.

[73] Assignee: International Business Machines Corporation, Armonk, N.Y.

[21] Appl. No.: 173,400

[22] Filed: Dec. 23, 1993

[51] Int. Cl.6 ............................................... H04N 7/18
[52] U.S. Cl. ..................................... 348/126; 348/130; 382/147
[58] Field of Search ....................... 348/130, 126, 87; 382/8; 356/394

[56] References Cited

U.S. PATENT DOCUMENTS

| | | | |
|---|---|---|---|
| 3,824,588 | 7/1974 | Vermillion | 340/347 |
| 3,891,930 | 6/1975 | Petrussen | 328/117 |
| 4,380,757 | 4/1983 | Vancsa | 340/347 |
| 4,454,539 | 6/1984 | Fedde et al. | 348/126 |
| 4,587,617 | 5/1986 | Barker et al. | 348/126 |
| 4,651,105 | 3/1987 | Inbar | 328/150 |
| 4,724,378 | 2/1988 | Murray et al. | 324/73 |
| 4,829,236 | 5/1989 | Brenardi et al. | 324/73 |
| 4,947,169 | 8/1990 | Smith et al. | 341/121 |
| 5,003,196 | 3/1991 | Kawaguchi | 307/290 |

Primary Examiner—Tommy P. Chin
Assistant Examiner—A. Au
Attorney, Agent, or Firm—Perman & Green

[57] ABSTRACT

A calibration system for circuit inspection tools in which analog threshold levels are automatically set by digital signals. The inspection too includes an optical detector system that provides video signals to channels each containing an analog processor. In the analog processor an analog reference signal, an analog video inspection signal which may contain a defect indication and a digital threshold signal are employed. The digital threshold signal is converted into an analog threshold signal which is summed with the analog reference signal that has been inverted. The inverted, thresholded reference signal is then summed with the analog video signal. The summed analog video signal and thresholded reference signal is compared with a zero level. If the sum is greater than zero a defect is indicated.

6 Claims, 6 Drawing Sheets

FIG. 1A.
FIG. 1B.
FIG. 1C.
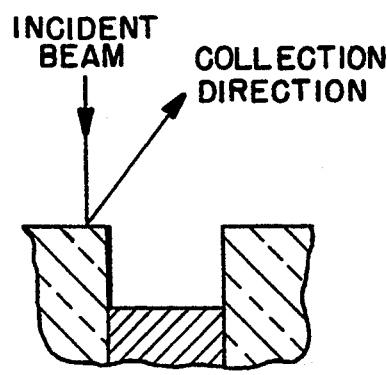
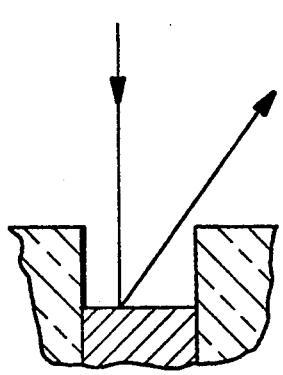
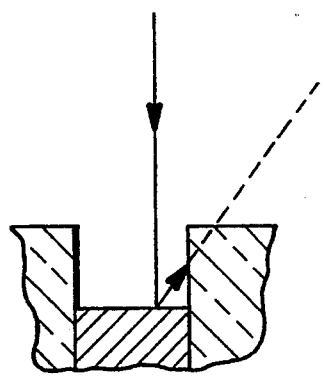
FIG. 2.
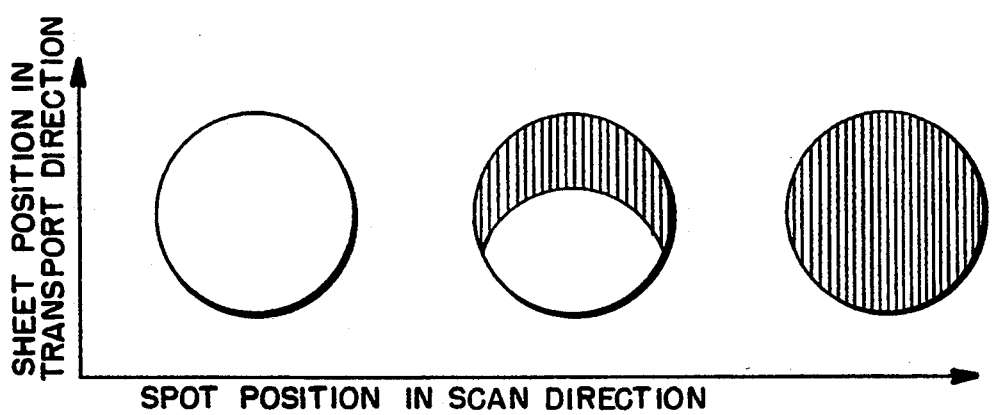
FIG. 3.
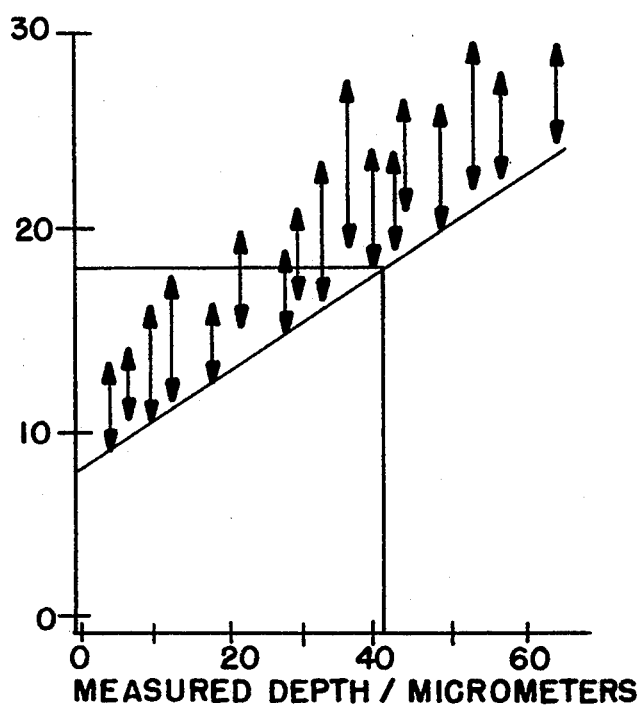

FIG. 4A.
P/F
FIG. 4B.
PIT
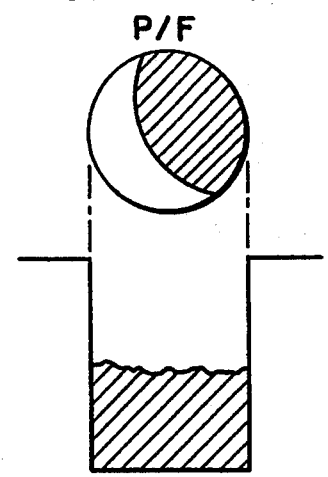
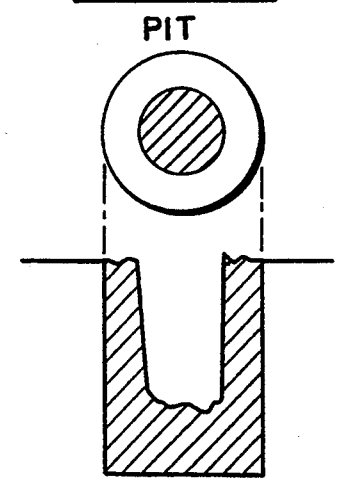
FIG. 5.
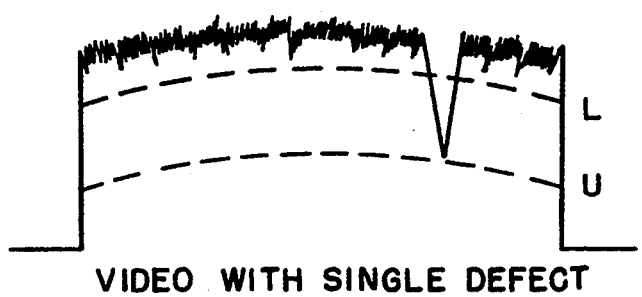
VIDEO WITH SINGLE DEFECT
FIG. 6.
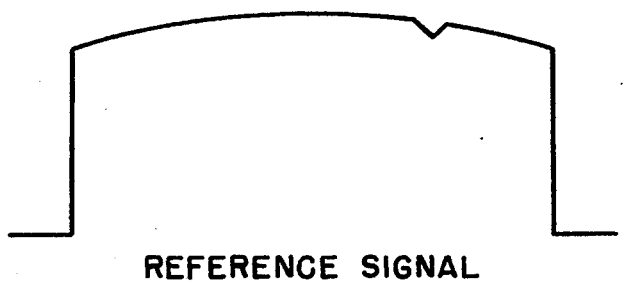
REFERENCE SIGNAL
FIG. 7.
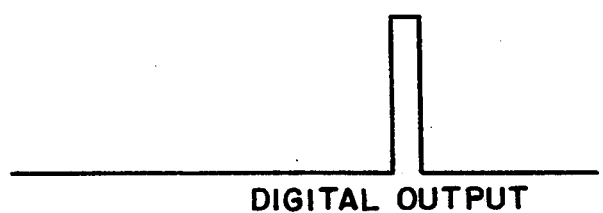
DIGITAL OUTPUT

AUTOMATIC THRESHOLD LEVEL STRUCTURE FOR CALIBRATING AN INSPECTION TOOL

BACKGROUND OF THE INVENTION

1. Field of the Invention

The present invention relates to inspection systems for inspecting electronic components, and more particularly to an automatic calibration system for setting threshold levels in an inspection system.

2. Background Art

U.S. Pat. No. 4,724,378 issued Feb. 9, 1993 to Murray et al and entitled CALIBRATED AUTOMATIC TEST SYSTEM discloses a calibrated automatic test system including a test station for generating digital test function codes and a test head containing a plurality of I/O pins for connection to a device under test. Each I/O pin includes a pin electronics circuit responsive to the digital test function codes for providing test signals to the device under test. The pin electronics circuits are inexpensive CMOS IC's and lack the accuracy needed to test VLSI devices at the frequencies of interest. An external calibration unit is connected to each I/O pin and data measurements are taken which represent the performance of the CMOS IC's. The data measurements are converted to calibrated function codes representing desired data values which are then stored in correction memory circuits which respond to nominal digital test function codes and substitute in their places calibrated function codes which are then supplied to the pin electronics circuits.

U.S. Pat. No. 4,651,105 issued Mar. 17, 1987 to Inbar entitled DIGITAL PEAK DETECTING MEANS FOR A PULSE TRAIN OF ELECTRICAL SIGNALS HAVING A FREQUENCY WITHIN A KNOWN FREQUENCY BANDWIDTH describes a digital peak detecting circuit for receiving a pulse train of electrical signals having a frequency within a known frequency range and for converting the same into digital signals is shown. The digital peak detecting circuit includes an input circuit having a phased-locked loop for producing clock pulses at a frequency which is a preselected integer of the electrical signals frequency and for deriving therefrom an analog input signal. A pulse control circuit receives and counts a predetermined number of clock pulses and produces count enabling signals. A peak detecting circuit is provided which includes a comparator which has the analog input signal and a analog output signal voltage applied to the inputs thereof and which has an output coupled to the pulse control circuit. A digital counting circuit is responsive to count enabling signals by changing count direction and produces discrete digital output signals which are stored in a latch register at the time the digital counting circuit changes its count direction. A digital-to-analog converter produces the analog output signal voltage and it is applied to the comparator input for comparing the analog input signal with the analog output signal voltage and the comparator enables the digital counting circuit as long as the analog input signal is of a greater magnitude than the analog output signal voltage, and when this condition is reversed, the digital counting circuit is reversed in counting direction, and the binary value thereof is stored in the latch register.

U.S. Pat. No. 4,380,757 issued Apr. 19, 1983 to Vancsa and entitled DATA ACQUISITION SYSTEM AND ANALOG TO DIGITAL CONVERTER THEREFOR describes a system in which, from a plurality of parallel channels of communication, each including a voltage-to-frequency (V/F) converter, a central clock synchronously timed for each channel, the derivation of a train of pulses having a number of pulses representative of the magnitude of an analog signal inputted to the V/F converter. The central clock also times the multiplexing at the measuring point of either the analog input signal or a bias voltage for calibration or a voltage reference for sealing. The central processor receives the counts from each train of pulses, combines them and threats them to provide a corrected count in each channel separately. Clocking and pulsing are effected through an isolation transformer associated with each channel, to and from the central processor.

Other patents which illustrate various other testing, detecting, and digital-to-analog converting and other circuits available in the art are as follows: U.S. Pat. No. 5,053,770; 5,003,196; 4,947,169; 4,829,236; 3,891,930; and 3,824,588.

SUMMARY OF THE INVENTION

An object of the present invention is to provide improved automatic calibration means for circuit inspection tools.

Another object of the present invention is to provide an improved calibration means for inspection tools wherein analog threshold levels are set automatically.

A further object of the present invention is to provide an improved calibration means for inspection tools wherein analog threshold levels are automatically set by means of digital signals.

The foregoing and other objectives, features and advantages of the present invention will be more readily understood upon consideration of the following detailed description of the invention taken in conjunction with the accompanying drawings.

FIGS. 1A, 1B and 1C illustrate the progress of a light spot hitting on a via in an inspection tool employed in an embodiment of the present invention;

FIG. 2 is an illustration of a filled hole, a partially filled hole and a deep hole as detected by the inspection tool employed in the present embodiment;

FIG. 3 is an illustration of a calibration curve used in the discussion of the present invention;

FIGS. 4A and 4B are illustrations of the shadows produced by a partially filled via and a via with a pit.

FIGS. 5, 6 and 7 are illustrations of a video signal of a defect, a reference signal and a digital output signal used in the discussion of the present invention;

DETAILED DESCRIPTION OF THE INVENTION

Figure 8:
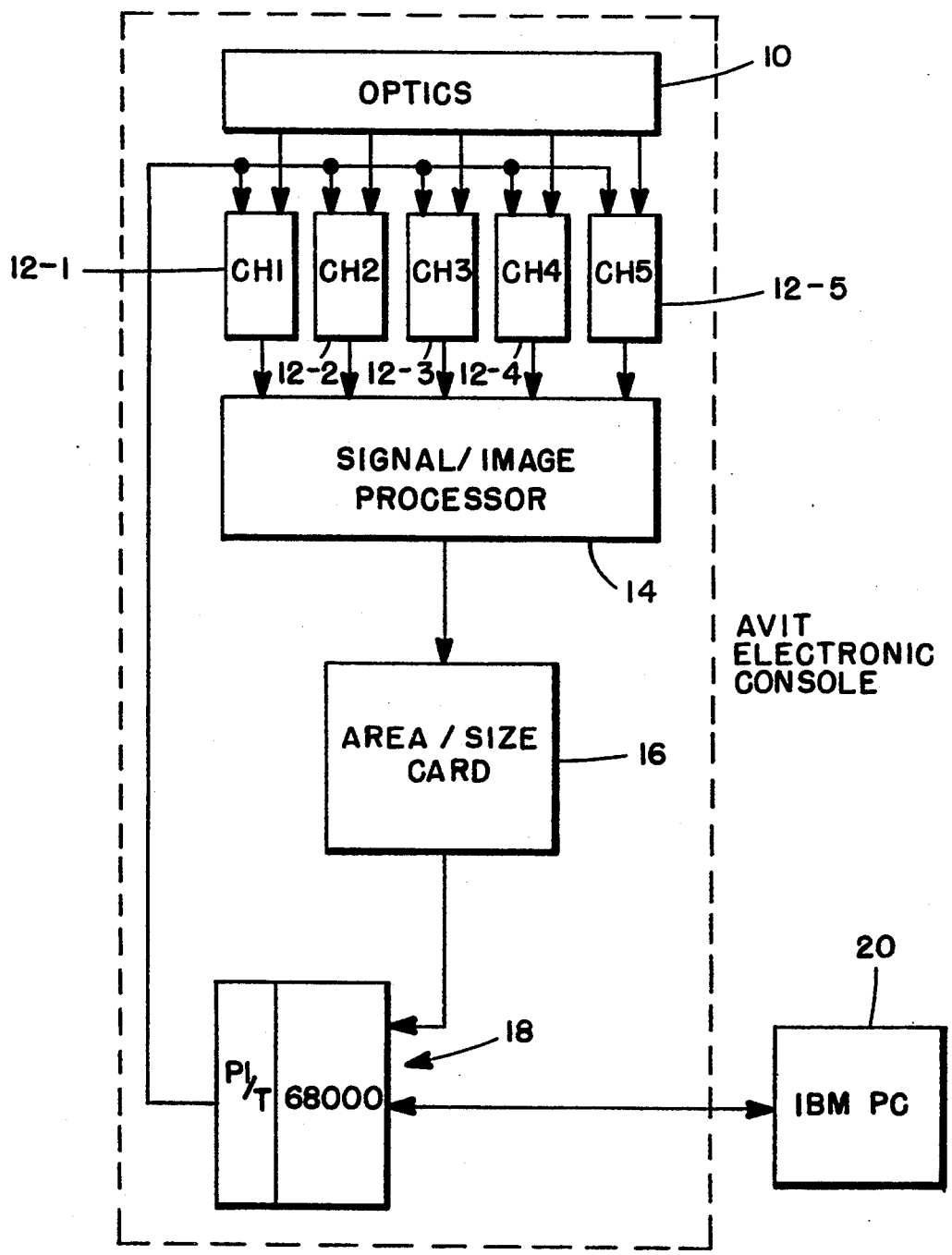
FIG. 8 is a schematic block diagram of an inspection tool for which the present invention provide improved, automatic calibration.

In the fabrication of integrated circuits, inspection tools are widely used to determine whether the circuits have been manufactured according to specification. Particular elements of an integrated circuit which undergoes inspection are the vias, which are the plated conductive holes in the integrated circuit boards that interconnect the various levels or planes of the circuits.

The calibration structure for threshold setting of the present invention will be described with respect to an advanced via inspection tool (AVIT).

The AVIT inspects vias on unfired ceramic layers used in microelectric packaging for paste fill depth, spacing, and size. Four shadow images from different angles and one vertical image determine the fill status of 100,000, 89 um vias in the area of 160 mm by 160 mm. Each via is filled with a conductive paste.

The paste depth is determined by the area of shadow give by each oblique direction. The greater are of shadow is used to determine via depth. The AVIT incorporates a laser scanner, rotating at 28,500 rpm, telocentric scan lens, and dedicated signal processing, one of the electronic racks uses ECL running at 87 MHz. The other electronics are predominant Fast-TTL.

The AVIT telocentric laser scanning front-end is used to produce a 633 nanometer, twenty micron spot scanning spot scanning at 3800 scans per second. A passive wobble correction is designed into the optics to null out any tracking errors from the polygon rotating at 28,500 rpm. The optics provide a 170 mm scan so the entire sheet can be inspected in one pass. The light reflected off the greensheet is collected by 4 fiber bundle assemblies (2 for and 2 aft of the scan line), and one in retro-reflection and each fiber bundle assembly consists of 420 fibers arranged in 2 rows of 210 each. These 1 mm fibers collect the light at the sheet and relay it to the PMT's located in an adjoining housing and these bundles work in pairs. The channels 1 and 2 detect fore and aft of the scan and 42.4 degrees off the sheet. These are positioned to detect partial-filled vias down to 40 micron depth. The channel 3 and 4 are positioned 59.7 degrees off the sheet. They are optimized for detection in the 70 micron depth region. Using the ceramic level as 100% reflective then the paste will generate a 60% level and obscuration (shadow) a 10% reflectivity level. These angle channels detect the obscuration from a partial fill or empty via. The system collates this obscuration data to determine if a feature displays enough pixels to be classified as a defect.

FIGS. 1A, 1B and 1C illustrate the progress of light spot hitting on a via. In FIG. 1A the light spot falls on the ceramic surface. In FIG. 1B the light spot falls on paste and in FIG. 1C the light spot falls on paste and is concealed from the light collector and the signal is zero. FIG. 2 shows, from left to right, a completely filled hole, a partially filled hole and a deep hole.

The fiber bundles provide the information to detect flaws in the Z axis. The fifth channel provides the information for detection in the horizontal plane. The fifth channel collects the laser light in retro-reflection utilizing a hole-in mirror beam splitter. This allows the focusing laser light to pass through the hole to the sheet and reflects the returning light to a set of collecting optics to be focused onto a single fiber.

The fifth channel detects contrast between the ceramic and paste or debris. The threshold signal is then used to build a pixel map of the feature. A box is built around the feature and the X/Y limits are determined based on the box dimensions. This is to determine if a via has exceeded a preset limit in either axis. From this information a boundary is set on the trailing edge in scan and machine direction. Software adjustable perimeter defines the area that should be object-free. If any feature is written into this area it will be classified as a spacing defect. The system also checks for features that are less than a preset limit in area. This is to detect debris on the sheet that could cause shorts when making contact with the next layer. This is the only defect limit that is set in hardware.

In order to detect partial-filled vias a calibration curve as shown in FIG. 3 is needed to select the proper threshold. FIG. 3 shows the area of shadow measured versus manual depth measured. The area of shadow is measured from channel 1 and channel 2 and the minimum value will be chosen as we discussed above. If the calibration is too sensitive, the system will lose accuracy for shallow via and scatter of the curve will be large. If the calibration is not sensitive enough, there will be no distinction between shallow and deep partial-filled vias. Before running the system at manufacturing the calibration of the system is the most important task to do. The process specification of partial-filled vias is a depth greater than 40 micron. From FIG. 3 the shallow lower threshold will be chosen by mapping from 40 micron depth in x-axis.

The pit detection is strictly from channel 5. A via with a pit has more shadow area than a partial-filled via as seen by channel 5 as shown in FIGS. 4A and 4B. The area of via less than 41 micron depth which be less than the shallow lower threshold picked from FIG. 3 will be called as good via. And the area of via greater than the shallow upper threshold will be called as unrepairable via. The other vias falling on between shallow lower threshold and shallow upper threshold will go to a pit decision means to decide whether it is a pitted via or repairable via.

After optically scanning the vias, the optical signals are applied to the system processors.

The electronic processing system for AVIT can be divided into five main sections as follows:

a. Receiver Box:
    PMT (Photomultiplier tube) and preamplifier
    SOS (Start of Scan)
    EHT control
    Laser control and monitor b. Analog Rack:
    Analog controller
    Analog processor c. Fast Buffer Rack:
    Fast Buffer controller
    Fast Buffer card d. Feature Extractor Rack:
    Master card
    Slave card
    X-Y card e. Parameter Combination Rack:
    68000 card
    VME interface
    Area
    Size
    Spacing Violation Input FIFO
    Spacing Violation Logic-Joint
    Bit Memory These sections are discussed in more detail as follows.

a. Receiver Box

This unit contains the PMT and preamplifier circuits, which convert optical signal to electrical signal and then convert the current output to a voltage signal to be driven down coax-cable to analog processor as the input. The PMT for the AVIT is a Thorn EMI type 9850B, a 6-stage tube that operates at frequencies over 200 MHz with a gain of 1 A per lumen at an output current of 0.2 mA. The preamplifier is a standard circuit with an operating bandwidth about 40 MHz with the signal-to-noise ratio greater than 30 dB, corresponding to 3% noise at the output.

b. Analog Rack

Analog processor electronics are fairly simple, consisting of the thresholds of the signal at two levels, approximately 30% and 85%. FIG. 5 shows a typical signal with the threshold levels. There are five analog processor for processing each of the five video signals. The processor card converts the analog video signal into a digital signal by using a threshold technique. The video is compared with a stored reference version of a video (FIG. 6) and a digital output (FIG. 7) generated each time the threshold is crossed as shown in FIG. 8. The unique feature of this threshold technique is that there are a good set of analog signals even though the reference level was not perfectly flat. Each processor has two thresholds: a black level (shadow) threshold used for channels one to four, and a grey level (paste) for the fifth channel.

The video is passed through a switched filter to band-limit the video to around 100 KHz. The filter is switched at the leading and trailing edges to a smaller time constant to allow the signal to rapidly reach the average level. The signal can now be digitized every 4 us (250 KHz) and stored in memory, 2 Mbyte capacity with 250 nsec access time. While the sheet is being inspected, this reference signal is played back through a D/A converter and a variable gain stage to remove imperfections in the pedestal and give an adjustable threshold which is summed with the incoming video to produce the digital signal corresponding to grey and black levels on the video signal.

The Analog Controller circuit has three functions. First it provides the interface to the transport system, terminating the 'sheet in' and 'inspect signals' and generating the 'sheet hold' signal. Secondly it interfaces the electronics cabinet to the receiver box by terminating the 'start of scan' signal and generating the 'EHT hold' signal. Thirdly, it generates all the common control signals required by the analog processor cards and somerseted signals required by other electronic processing racks.

c. Fast Buffer Rack

The fast buffer cards store the coordinates of the edges of the channel signals; they are able to store this information at a very high burst rate, 11.53 ns period (86.7 MHz) and 1024 features maximum. The stored information can be read at a much slower rate by the feature extractor, 328 ns per feature. To enable both reading and writing to take place simultaneously two memories (1024×16 bits each) are used, one being written to while the other is being read, their function being switched from scan to scan. The fast buffer cards only respond to positive edges. To process both rising and falling edges of the features the fast buffers are arranged in pairs with the normal and inverted differential 'latch rising edge' signals reversed between the pairs.

The electronics are implemented entirely in ECL technology as, although faster TTL can be clocked at around 100 MHz, the propagating delays slow up the throughput of data and cause severe synchronization problems.

The fast buffer controller generates all the common control signals required by the fast buffer cards. These are generated from an 86.7 MHz (11.53 ns) master clock which is synchronized to the start of scan signal. This clock frequency gives square pixels when the spinner is rotating at 28500 rpm. All signal inputs from the analog controller are received on this card, synchronized to the master clock and combined to generate the master channel data.

d. In the feature extractor rack data from a via is collected on a line-by-line basis; however the results are required on a per via basis. The data from each via on every line must therefore be linked to data from the same via on adjacent lines. Conventional image processing systems deal with this type of problem on a frame-by-frame basis, waiting for all the data to be collected. This process is not practical in this case, however, as the image from the system would be greater than 16000 pixels square.

The data required from each via is as follows:
a. the x and y bounds of the via
b. the area of via
c. the x and y bounds of the shadow area
d. the area of the shadow (black) area The system has to deal with up to 800 pairs of coordinates in a single scan time. This gives approximately 400 ns per pair of coordinates.

The master card processes edge data taken from the fast buffer master card. It stores the edges in a FIFO and outputs the coordinate of the last edge to all the slave cards when all five slaves have finished processing, the master card requests the next pair of edges from the master fast buffer and repeats until no more edges are left in the master fast buffer for the scan line. The master card then starts a new scan line and requests the first pair of edges and then checks with the first set of edges stored in the Fifo on the last scan. If they overlap, the are part of the same feature and are combined. If the edges both occur before the stored pair, they are stored as the start of a new feature. If the edges both occur after the stored pair, the previous feature is finished. Therefore, it updates the limits for a feature on the current line and then tells the slave processors to grab data within those limits and process. When all the slave processors have finished processing, the master processor then grabs more data, decides whether the feature is completed and if so, then controls the output of the coordinates to the next parameter combination rack.

The slave cards are all the same but are configured as either white or black slaves when the pcb is plugged into the rack. The channel 1 through 4 are the processing for black area and the channel 5 is the processing for white area. It contains the registers required to store hole size information under the control of the master channel. A 13 bit wide by 1024 deep FIFO forms a hole BLIP_HIGH coordinates to produce blip length. This is used to produce the hole area. By control of the master card and the feature is finished, it output the each area to parameter combination.

The X-Y card processes data from the white slave processor. It generates the Xmin, Xmax, Ymin, and Ymax coordinates for each feature. It has a 61 bit wide by 1K deep FIFO to save the hole coordinates from the previous scan line. If a new feature is started, the four coordinates are stored and if the feature is continued, the four coordinates are updated and stored.

e. Parameter Combination Rack

The parameter combination rack contains the size and area processing pcbs, the VME interface pcb and the 68000 processor pcb, which sends the thresholds to the size and area processing pcbs and receives the types and coordinates of defects to display at IBM PC/AT. The main function of the parameter combination rack is the size and area processing. There is one area pcb processing the five areas, four black and one white, calculated by the feature extractor. There are five pcbs processing for the size.

Figure 11:
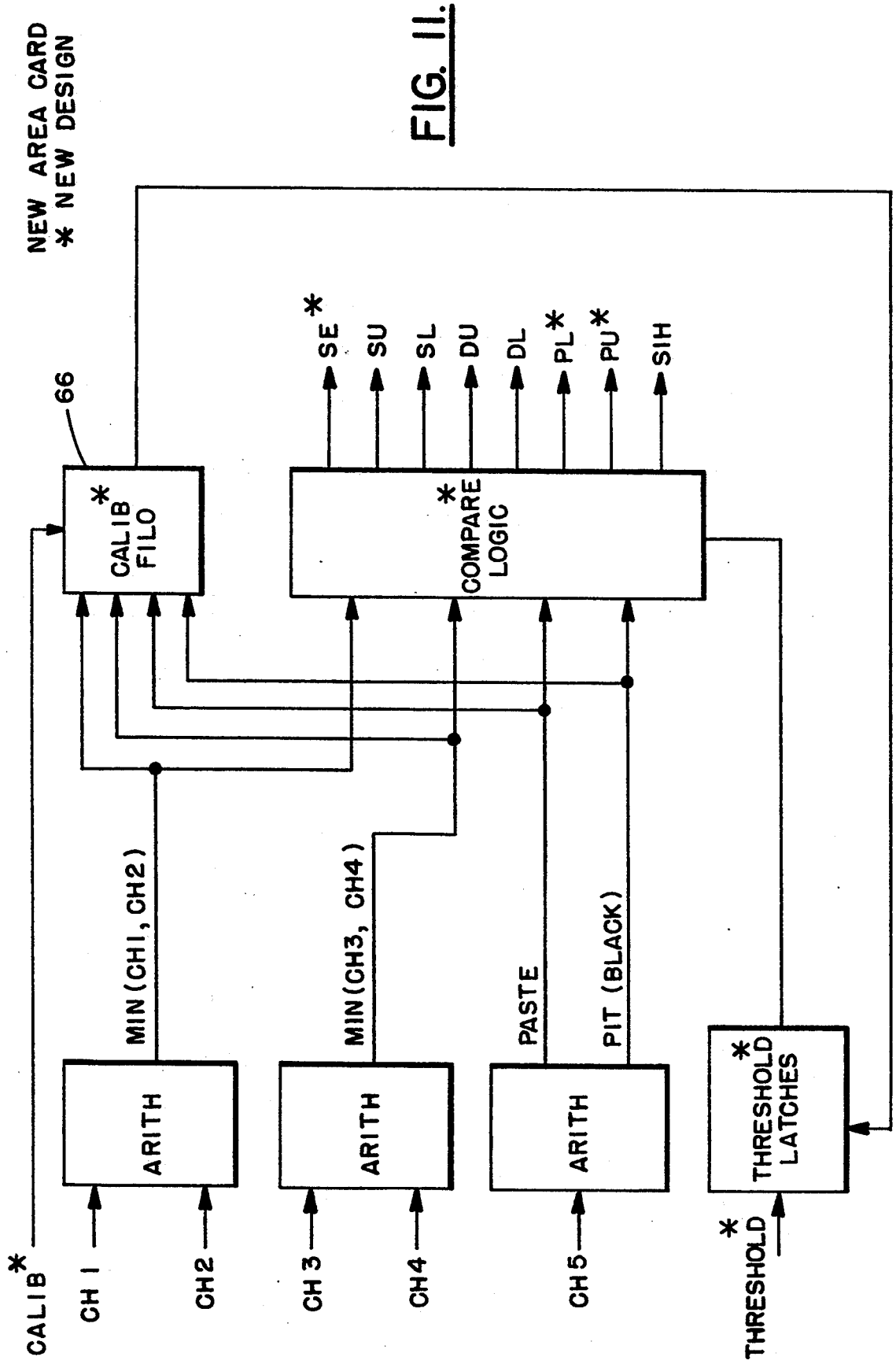
FIG. 11 is a schematic block diagram of an area parameter circuit user in the present invention.

The area circuit, the details of which are shown in FIG. 11 and will be later discussed, processes the four black and one white area generated by the feature extractor, and compares them with computer set thresholds to provide five defect signals which are further processed on the size card. There are three area processing at the area circuit. One is the deep channel black area processing, which generates 11 bits long, the twelfth bit being set if the area overflows. Other one is the shallow channel black are processing, which is exactly the same as for the deep black area except that the signals are generated by the more horizontal pair of optical fiber bundles. The last one is the white area processing, which compares the number with the computer set threshold and output a defect, called as substrate in hole, if the level is exceeded.

Figure 10:
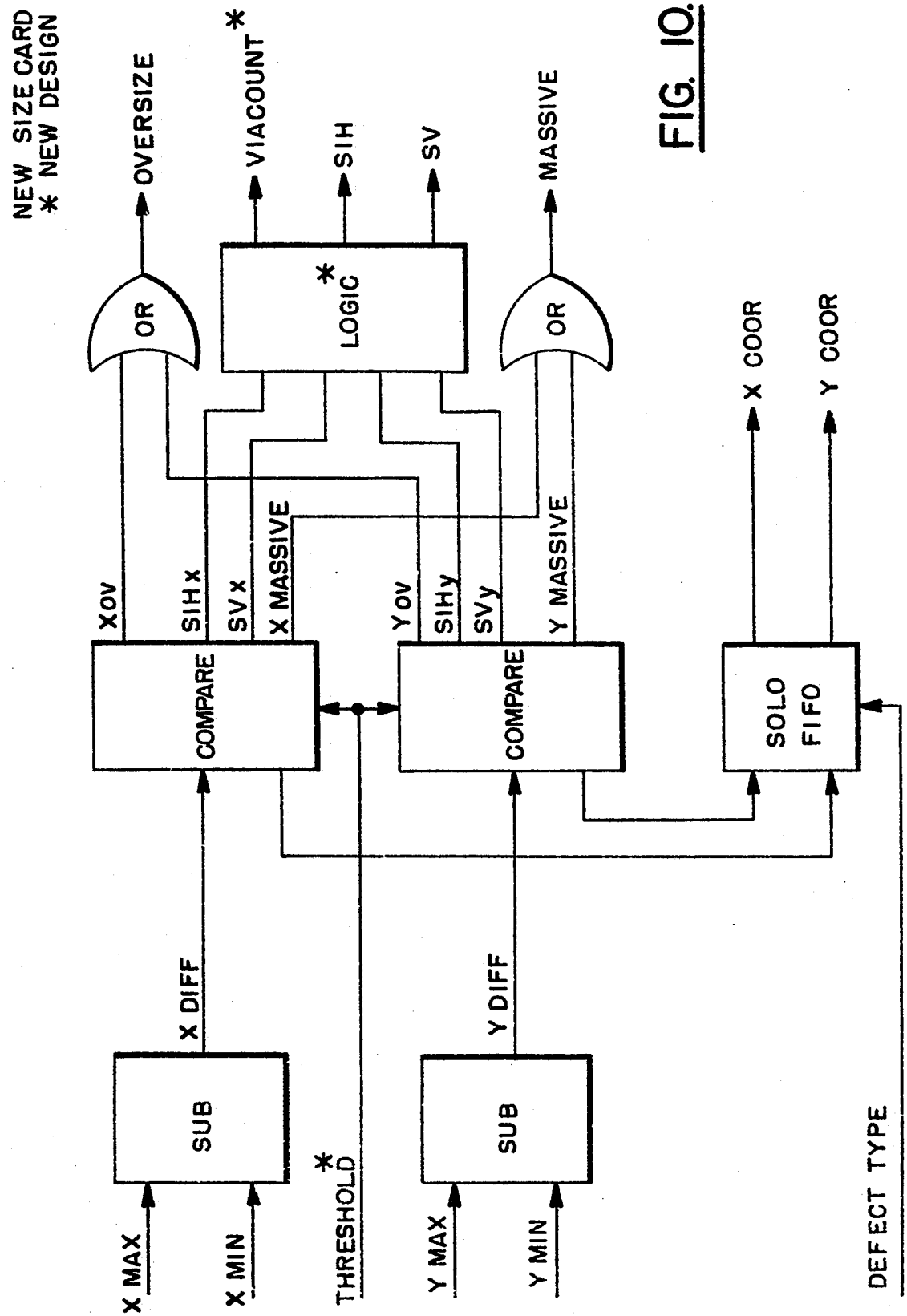
FIG. 10 is a schematic block diagram of a size parameter circuit used in the present invention.

The size circuit, the details of which are shown in FIG. 10 and will be later discussed, processes the X and Y coordinates of each feature from feature extractors and compares the result with the computer set threshold to give an oversize defect signal. It also compares the result with a fixed threshold which defines whether the coordinates are sent to the spacing violation processing or whether they are too large. All defects such as underfilled, empty, and substrate-in-hole will be stored at the solo FIFO. And it sends the Xmax, Ymax, Ymax, Xdiff and Ydiff to the Spacing Violation Input FIFO circuit for the spacing violation check.

The via limits arrive in the input FIFO from size card and the computer spacing violation threshold. The FIFO is 42 bits wide and 32K deep and enables the spacing violation processing to operate at its own speed without losing any data. This circuit also has two sets of adders used for adding the spacing criterion onto the X and Y coordinates.

The spacing violation logic and joint logic cards contain a system controller which sequences the operations of the various circuits on the card. Several of these circuits control the bit memory, the are: address counters, read and write signal generators, a clear address counter and clear write signal generator, a circuit for deciding whether or not the whole of the bit memory requires clearing and a circuit for selecting which of the eight bit memory banks are to be used. It controls the bit memory card and draws the via data in bit memories.

The spacing violation bit memory is simply a band of memory cards. There are two identical cards, such as bit memory 1 and bit memory 2. Each bit memory band consists of 4, 32K × 8 bit, IC's giving 32K bit for each band. A feature is written a bit at a time under the control of the X/Y addresses from the logic and joint card. It checks for a spacing violation and flags the violation and store at the joint FIFO in logic and joint card if it occurs.

The VME interface is a general purpose interface between the processing electronics and the VME bus. The pcb provides 8 read and 8 write data strobes each for 16 bit data. A single level interrupt is also implemented. A status register is included at the first read address and a control register at the first write address. The fault processing and latching is also contained on the card and this is located at the second read address.

FIG. 8 illustrates a system block diagram of the components of an advanced via inspection tool AVIT presently employed in manufacturing integrated circuits and described hereinabove. The basic elements of the via inspection tool include the optics and receiver box portion 10 that optically views the via and provides the five video channels. A plurality of analog processors (analog rack) are arranged in five channels and are shown as 12-1, 12-2, 12-3, 12-4 and 12-5. The analog processors provide inputs to a signal/image processor 14 which in turn provides an input into an area and size circuits 16. The output from the area and size circuits 16 are applied to a processor means 18.

Thus far, FIGS. 1 through 8 and the description thereof relates to a via inspection tool known in the art. As previously stated, the present invention is an improvement to the inspection tool wherein threshold levels are automatically set by digital signals. In conventional AVIT systems heretofore, the threshold levels are set by mechanically tuning and setting potentiometers.

Figure 9:
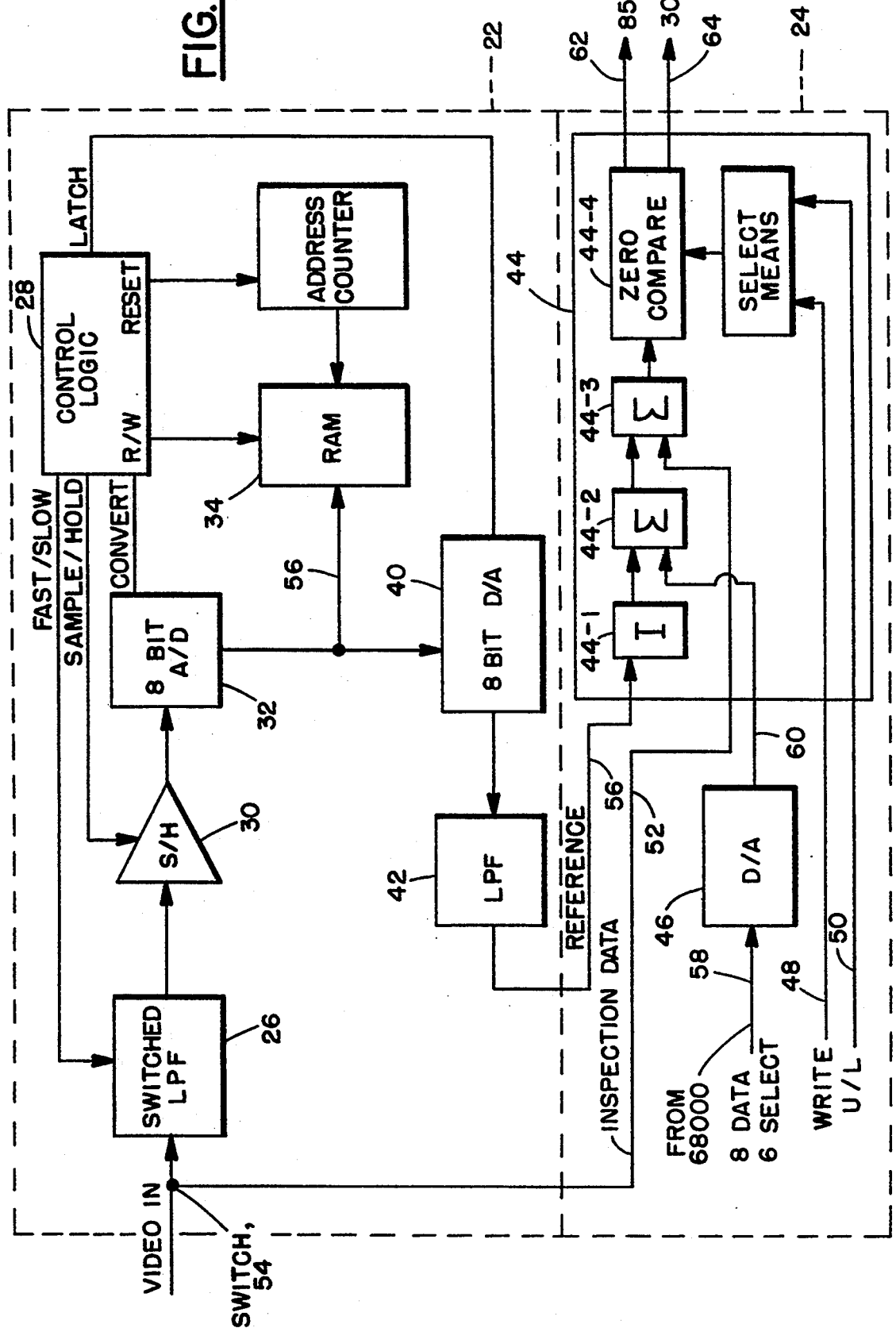
FIG. 9 is a schematic block diagram of an improved analog processor employed in the inspection tool of FIG. 1 according to the principles of the present invention.

Referring to FIG. 9, a schematic block diagram is shown illustrating the components contained in each one of the analog processors 12-1, 12-2, 12-3, 12-4 and 12-5 associated with each of the five video channels shown in FIG. 8. The portion of FIG. 9 designated 22 contains the logic, processing and memory means found in a conventional analog processor of an inspection tool according to FIG. 8. The function of the elements in section 22 is to provide a reference signal for purposes of comparison. The elements shown in circuit portion 24 illustrate an embodiment of means for automatically setting the analog thresholds during the calibration of the tool according to the present invention.

In circuit portion 22 of FIG. 9, a video signal from the optics 10 is applied as an input signal through switch 54. The video signal is obtained prior to starting the inspection process. It is used to establish a background reference prior to inspection and detection of any defects. The video signal is passed through a low pass filter 26 to remove high frequency noise from the video signal. Low pass filter 26 is controlled by a signal from control logic means 28 to operate either fast or slow, whichever is better in view of the type of signal noise in the particular channel in which the processor is in.

The output signal from low pass filter 26 is applied to a sample and hold circuit 30 under the control of the control logic means 28 to provide video signal samples to an 8 bit analog-to-digital converter 32 that converts the analog video signal to a digital signal under control of an enable "convert" clock signal from control logic means 28. The digitized video signal is then stored in RAM memory 34 in readiness for the inspection process.

When the inspection process starts the switch 54 is activated and the video signal obtained from the inspection by optics 10 is conducted on lead 52 to the threshold generator and level comparator means 44 in circuit portion 24. The video signal will contain inspection data such as a via defect, as depicted in FIG. 5. The reference signal is read at from RAM memory 34 and conducted back through lead 56 to an 8 bit digital-to-analog converter 40 where it is returned to analog form and passed through low pass filter 42. The reference signal output from filter 42, which is depicted in FIG. 6, is also applied to threshold generator and level comparator means 44 or lead 56.

Thus, a signal from the inspection process containing defect data (FIG. 5) and a non-defect data reference signal (FIG. 6) are applied to threshold generator and level comparator means 44.

Also in circuit portion 24, a 14 bit signal from the 68000 processor is conducted on lead 58 to a digital-to-analog converter 46. In the signal, 8 bits are data bits that specify the desired threshold level, and 6 bits identify the particular channel of the five processor channels. The analog signal from converter 46 is applied to threshold generator and level comparator means 24 on lead 60.

Within threshold generator and level comparator means 44 the reference signal on lead 56 is inverted by inverter 44-1 and added to the threshold level signal on lead 60. This provides an inverted thresholded reference signal by summing circuit 44-2 which is then summed with the analog video signal with the defect data (on lead 52) at summing circuit 44-3. The inverted reference signal cancels out the video signal. The summed signal is compared to a zero level at comparator 44-4, and if the summed signal is greater than zero, a defective via exists and has been detected.

Depending on which of the five channels in which processor is connected, as indicated by the 6 select bits on lead 58, either a high threshold or a low threshold will be generated depending on a "U" (upper threshold) or "L" lower threshold signal to threshold generator and level comparator 44 on lead 50. The upper "U" and lower "U" threshold levels are depicted in FIG. 5, and may be, for example, an 85% threshold value or a 30% threshold value. The "U" (85%) analog threshold signal, when selected, appears on lead 62 and the "L" (30%) analog threshold signal, when selected, appears on lead 64 from threshold generator and level comparator 44.

The operation of the circuit of FIG. 9, including the circuit portion means 24 for automatically setting the analog thresholds, is described in more detail as follows.

As previously stated, the present invention provides means wherein analog threshold levels are automatically set by means of digital signals instead of setting two potentiometers. There are 512 different combinations of the digital signal to setup the threshold levels. The way to set the analog threshold is as follows.

Before setting the analog threshold automatically, the testsheet which contains 40 to 100 known defects is needed. The defects are all partial-filled vias, with depth ranges from 25 um to 75 um, and the data is obtained from the inspection system. The following steps are then performed.

Step 1. Using conventional automatic calibration software from a data processor 20 (FIG. 8), which may be a personal computer, enter a proper range of thresholds such that the search performs as little iteration of the calibration process as possible.

Step 2. The inspection table cycles as the calibration starts automatically.

Step 3. A selected one of the range of starting thresholds given at procedure step 1 is sent to the 68000 processor of the AVIT.

Step 4. This selected threshold will be converted to 16 digital bits which consist of 8 for threshold data, 6 for to specify the channel and 2 for specifying an upper or lower threshold range.

As shown in FIG. 9, eight data bits from the 68000 processor go through D/A (digital-to-analog) converter 46 which will convert digital bits to analog signal. Six select channel bits from the 68000 will choose which channel is for the threshold and send the bits to D/A converter 46.

The U/L, line 50 in circuit portion 24 carries a control signal that selects the range of threshold level, which is, for example, 85% or 30%.

A write control (clock) signal on lead 48 is provided from to enable the thresholding process.

At the threshold generator and level comparator means 44, a reference signal from filter 42 on lead 56 is inverted by inverter circuit 44-1 and thresholded by summing it with the analog threshold data signal on lead 60 at summing circuit 44-2 and the inverted, thresholded reference signal is then summed with a raw video signal (from the inspection process) on lead 52 at summing circuit 44-3. And then the summed signal is compared with a zero level at zero compare circuit 44-4. If the summed signal level is greater than zero, there exists a defective via, but if the summed signal level is not greater than zero, there is no defect.

Depending on whether an upper or lower threshold range was specified on lead 50 for the channel in which the analog processor is located, a defect indication signal is produced on output lead 62 or 64.

The one of two outputs (upper or lower threshold range) on lead 62 or 64 is processed further in signal/image processor 14 (FIG. 8) depending on which channel 12-1, 12-2, 12-3, 12-4 or 12-5 is selected.

Once the area and coordinates of the via are determined, this data will be sent to the supporting Area/Size card circuits 16 (FIGS. 10 and 11). All defect data will be stored in Calib FIFO means 66 as shown in FIG. 11.

The process described herein above repeats and continues to select threshold value. Another threshold is automatically selected from the range given at Step 1 and the process described above is repeated again until the threshold is over the range.

Once the cycle is over, just as in the conventional AVIT, all the data will be collected at the 68000 processor and it is then passed to data processor 20 to analyze the data automatically. The data is analyzed in terms of the slope and the tightness of the data statistically such as correlation, and the like.

Thus, as in the conventional AVIT the best statistical data per threshold will be chosen automatically, and the chosen threshold is displayed. The different provided in the present invention is that the threshold values are determined automatically by digital signals.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. In an inspection system of the type wherein electronic circuit structures are optically scanned to produced video inspection signals containing data indicative of circuit defects, at least one processor means including threshold means for automatically setting analog threshold levels in response to digital signals comprising:

means for providing an analog reference signal representative of a video signal not containing any data indicative of circuit defects, means for providing a digital data signal having a value representative of a desired threshold level, a first digital-to-analog converter means connected to said digital data signal means for converting said digital data signal to an analog signal representative of said desired threshold level, means for providing a video inspection signal containing inspection data indicative of at least one circuit defect, a threshold generator and level comparator means including an invertor circuit and a first summing means and responsive to said analog reference signal and said analog threshold level signal for inverting said analog reference signal and summing it with said analog threshold level signal, to provide an inverted, thresholded reference signal, said threshold generator and level comparator means further including a second summing means responsive to said inverted, thresholded reference signal from said first summing means and said video inspection signal for summing said inverted, thresholded reference signal and said video inspection signal, and wherein said threshold generator and level comparator means further includes a comparison means connected to said second summing means for comparing the output signal therefrom to a zero level and producing a defect indication signal when said output from said second summing means is greater than zero and therefore greater than said desired threshold level.

2. An automatic analog threshold setting means for an inspection system according to claim 1 wherein said means for providing an analog reference signal includes an analog-to-digital converter circuit responsive to an analog video signal that does not contain inspection data for converting said analog video signal to a digital signal, memory means connected to said analog-to-digital converter for storing said digital signal, a second digital-to-analog converter means connected to said memory means, and a control means connected to said memory means for taking said digital signal from said memory means to said second digital-to-analog converter means to provide said analog reference signal from said second digital-to-analog converter means.

3. An automatic analog threshold setting means for an inspection system according to claim 2 wherein said digital data signal having a value representative of a desired threshold level is a high threshold level signal or a low threshold level signal, and wherein said inspection system further includes means for providing a signal to said threshold generator and level comparator means designating that said digital data signal having a value representative of a desired threshold level is a high threshold signal or a low threshold signal.

4. An inspection system of the type according to claim 3 wherein said at least one processor means in the inspection system includes a plurality of processor means arranged in separate channels, and wherein selected ones of said processor means include a high threshold level signal and other selected ones of said processor means include a low threshold level signal.

5. An inspection system of the type according to claim 3 wherein the circuit structures that are optically scanned are ceramic boards containing vias, and wherein said means for providing a video inspection signal contains inspection data indicative of flows in at least one via.

6. An inspection system of the type according to claim 3 wherein said means for providing an analog reference signal includes a low pass filter responsive to said video inspection signals for removing high frequency noise, a sample and hold signal circuit connected to the output of said low pass filter for sampling the analog video signal therefrom, said sample and hold circuit being connected to the input of said analog-to-digital converter circuit for providing said analog video signal thereto.

* * * * *